United States Patent [19]

Sherk et al.

[11] Patent Number: 4,589,957
[45] Date of Patent: May 20, 1986

[54] MONOMER AND DILUENT RECOVERY

[75] Inventors: Fred T. Sherk; Donald O. Hanson, both of Bartlesville, Okla.

[73] Assignee: Phillips Petroleum Company, Bartlesville, Okla.

[21] Appl. No.: 526,254

[22] Filed: Aug. 25, 1983

[51] Int. Cl.$^4$ .............................................. B01D 3/00
[52] U.S. Cl. ........................................ 203/75; 203/77; 203/78; 203/82; 203/87; 203/DIG. 19; 203/99; 526/348; 159/DIG. 18
[58] Field of Search .................... 203/71, 81, 82, 98, 203/DIG. 19, 80, 99, 73–75, 77, 78, 87; 526/352, 348.5, 922, 348; 208/354, 355; 159/DIG. 18; 196/99

[56] References Cited

U.S. PATENT DOCUMENTS

| | | | |
|---|---|---|---|
| 1,957,818 | 5/1934 | Carney | 203/82 |
| 2,290,442 | 7/1942 | Metzl | 203/55 |
| 2,325,379 | 7/1943 | Durrum | 203/55 |
| 2,339,576 | 1/1944 | Luten, Jr. | 203/34 |
| 2,751,422 | 6/1956 | Nelson et al. | 203/30 |
| 2,910,412 | 10/1959 | Muller et al. | 203/85 |
| 3,132,078 | 5/1964 | Backlund | 203/81 |
| 3,247,267 | 4/1966 | Brown | 203/81 |
| 3,280,091 | 10/1966 | Dance | 203/80 |
| 3,313,724 | 4/1967 | Kniel | 208/340 |
| 3,324,090 | 6/1967 | Ross et al. | 203/81 |
| 3,402,124 | 12/1968 | Jones | 208/353 |
| 3,642,731 | 11/1972 | Tegge et al. | 203/71 |
| 3,700,566 | 10/1972 | Bellinger et al. | 203/1 |
| 4,163,695 | 8/1979 | Archerd | 203/82 |
| 4,339,623 | 7/1982 | Morgan et al. | 203/DIG. 19 |

OTHER PUBLICATIONS

*Chemical Engineering Progress*, vol. 66, No. 8, Aug. 1970, pp. 54–60.

*Primary Examiner*—S. Leon Bashore
*Assistant Examiner*—V. Manoharan
*Attorney, Agent, or Firm*—Howard D. Doescher

[57] ABSTRACT

Improved process for the separation of a hydrocarbon-containing feedstream comprising monomer, comonomer and diluent into separate product streams which comprises subjecting the feedstream to two-stage distillation provided with a common accumulation zone wherein the condensate from the accumulation zone serves as the source of feed for the second distillation and reflux for the first distillation. In a specific embodiment, a feed comprising ethylene, 1-hexene, and isobutane is separated into separate streams of 1-hexene, ethylene and isobutane, and isobutane for recycle to polymerization.

9 Claims, 1 Drawing Figure

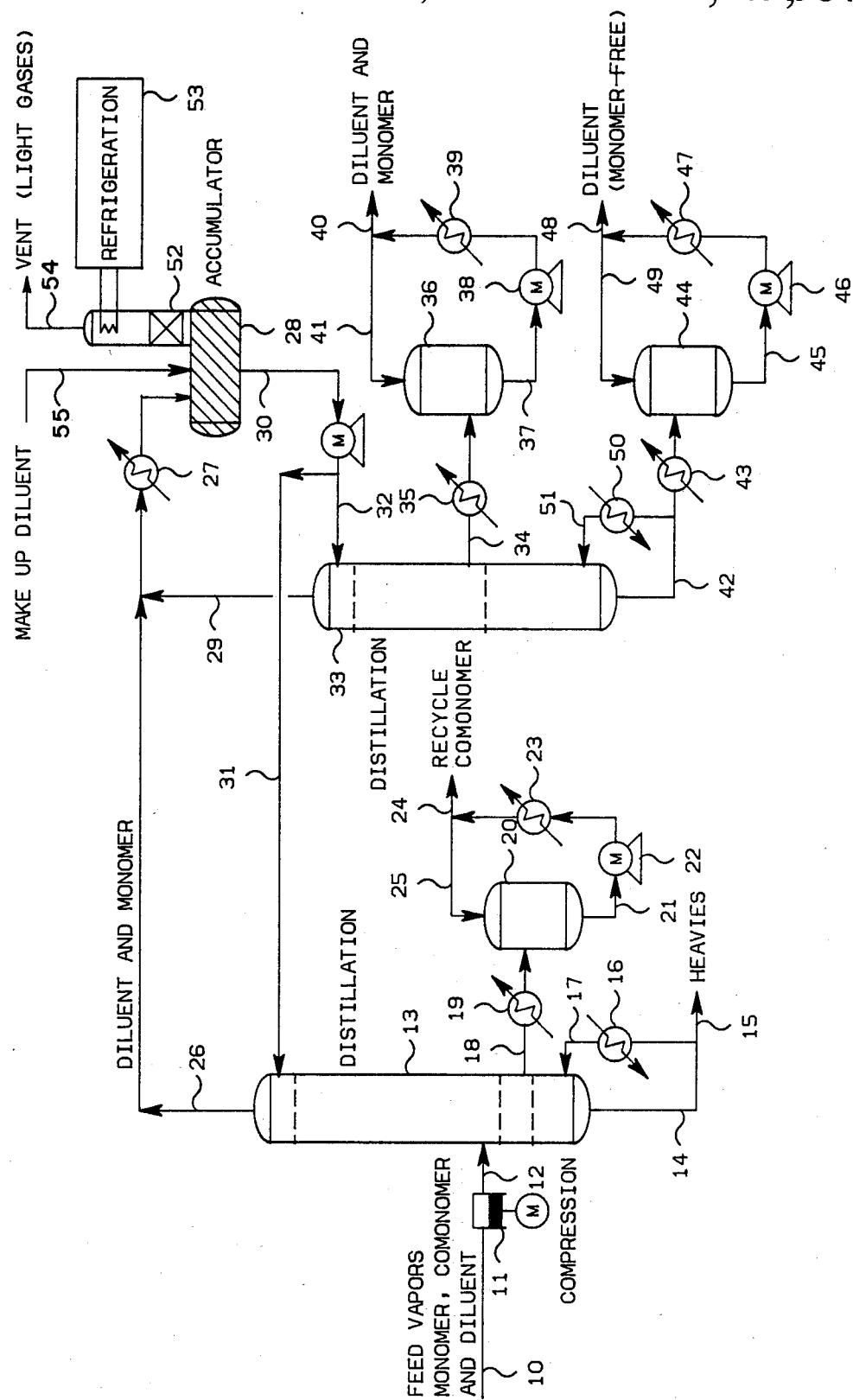

MONOMER AND DILUENT RECOVERY

This invention relates to the separation of hydrocarbon mixtures. In accordance with one aspect, this invention relates to the separation of a three component stream comprising monomer, comonomer and diluent. In accordance with a further aspect, this invention relates to the separation of a stream obtained from a polymerization process comprising monomer, comonomer and diluent in a distillation system having two distillation zones with a common accumulation zone and wherein the accumulated condensate from the distillation zones is used as feed and reflux for the respective distillation zones. In accordance with a further aspect, this invention relates to a recovery system comprising distillation wherein vapors recovered from a homopolymer and/or copolymer system are combined and separately recovered and used for recycle to the respective polymerizations.

It is known in the art to prepare thermoplastic materials by polymerizing unsaturated monomers to form high molecular weight normally solid thermoplastic polymers. Such polymers are frequently formed in the presence of a hydrocarbon diluent or solvent. Following polymerization the polymer can be separated from the hydrocarbon diluent and unreacted monomers by well known techniques, such as flash vaporization, stripping etc. Vapors recovered from the polymer reaction product whether by flash vaporization, stripping, or other means comprises diluent or solvent and monomer or monomers. It is highly desirable to separate the monomer, and in some instances comonomer, from the diluent in a manner such that high purity streams are separately recovered and which can be returned as recycle to the process from which these materials were separated.

The present invention is primarily directed to the separation of a vaporous stream having at least three components separated from the effluent from a homopolymerization and/or copolymerization process.

Accordingly, an object of this invention is to provide an improved process for the separation of vaporous hydrocarbon materials obtained from polymerization effluents.

Another object of this invention is to provide a process for separating monomer(s) from diluent in a more efficient manner.

A further object of this invention is to provide a separation system having reduced energy costs for operation.

Other objects, aspects, as well as the several advantages of the invention will be apparent to those skilled in the art upon further consideration of the specification, the drawing, and the appended claims.

According to the invention, a stream comprising monomer(s) and diluent is separated into individual monomer and diluent streams in a separation system comprising two distillation zones and a common accumulation zone wherein the overhead streams from both distillation zones are combined, condensed, the condensate is separated into a feed portion for the second distillation and a reflux portion for the first distillation, and separate streams of monomer and diluent are recovered for further use, e.g. recycle.

In a specific embodiment of the invention, a vaporous feedstream comprising monomer, such as ethylene, comonomer, such as 1-hexene, and diluent, such as isobutane, is compressed, subjected to distillation to separate a heavy bottoms stream and an overhead stream comprising monomer, comonomer, and diluent which overhead stream is condensed along with the overhead from a second distillation zone and the condensate formed from the combined streams is used for feed for the second distillation and reflux for the first distillation. A diluent stream substantially free of monomer and a diluent stream containing monomer are separated from the second distillation. Comonomer is separated as a sidestream from the first distillation.

The comonomer stream, the diluent plus monomer stream, and the diluent stream substantially free of monomer all can be recycled to a polymerization zone, whether homopolymerization or copolymerization depending upon monomers being subjected to polymerization.

The three-component stream separated according to the invention ordinarily with ordinarily be an overhead stream removed from a flash vaporation zone wherein a stream containing solvent, polymer and unreacted monomers is flashed or otherwise treated to remove solvent or diluent and monomers therefrom. A presently preferred three component stream separated according to the invention comprises monomer, such as ethylene, comonomer, such as 1-hexene, and diluent, such as isobutane. This stream can be obtained from the effluent from a copolymerization process and as a combined stream of ethylene and isobutene obtained from a homopolymerization process. It should be recognized that the separation system of the invention is equally applicable to other monomer, comonomer and diluent systems so long as feed vapors comprise hydrocarbons which permit separation by distillation.

While the invention is particularly valuable in recovering monomer and comonomer from a paraffinic diluent as described above the invention is broadly applicable for recovering monomers generally from admixture with diluent or solvent used in other polymerization processes. In particular, this invention is applicable to the recovery of monomer and diluent from systems producing polymers of ethylene, propylene and 1-butene, preferably with a mono-1-olefin of 5–10 carbon atoms per molecule as comonomer. Examples of such 1-olefin comonomers include 1-pentene, 1-heptene, 1-octene, 1-decene, 2-methyl-1-butene, 2-methyl-1-pentene, 3-methyl-1-pentene, 3-ethyl-1-pentene, 2-methyl-1-octene, and the like. These polymers can be prepared by any method known in the art, but presently it is preferred to recover monomers and diluent from polymer systems in which the polymer is produced in particulate or particle form. These polymers are ordinarily produced in a paraffinic hydrocarbon diluent, having a normal boiling point below that of the comonomer(s), such as n-butane, isobutane, 2-methyl-butane, n-pentane, 2-methyl-pentane, 3-methyl-pentane, and n-hexane.

The invention will be described further with reference to the drawing which represents a schematic flow diagram of the process of the invention and a representation of the apparatus useful therein.

Referring now to the drawing, feed vapors comprising monomer such as ethylene, comonomer such as 1-hexene, and diluent, such as isobutane, are introduced into the system by way of line 10 and passed to a compression zone 11 where the feed vapors are compressed to an elevated pressure and introduced by line 12 into an intermediate portion of distillation column 13.

The feed vapors in line 10 can be obtained from the recovery system of a copolymer plant used for the separation of monomer(s) and diluent such as used during the formation of ethylene/1-hexene copolymers. It is also within the scope of the invention to recovery monomer, such as ethylene, or other monomer and diluent, from a homopolymerization process and combine with the feed vapors in line 10.

Conditions obtaining within distillation zone 13 are such that materials heavier than 1-hexene, the comonomer, are removed from a lower portion of column 13 by way of line 14 and passed by way of line 15 to further recovery and/or use. A portion of the bottoms stream 14 is reboiled in steam-heated heat exchanger 16 and returned to a lower portion of distillation column 13 by way of line 17.

A side stream comprising comonomer is removed from column 13 by way of line 18 and passed through water-cooled heat exchanger 19 and to vessel 20. In this embodiment, the side stream comprises 1-hexene. 1-Hexene is removed from a lower portion of vessel 20 by line 21, passed through pump 22 and then water-cooled heat exchanger 23. A portion of 1-hexene is passed by way of line 24 for recycle to the copolymer plant and the remainder is returned by line 25 to vessel 20.

An overhead vapor stream comprising diluent and monomer is removed from distillation column 13 by way of line 26 and passed through water-cooled heat exchanger or condenser 27 and the condensate formed is passed to accumulator 28. An overhead stream 29 to be described later is combined with diluent and monomer stream 26 for passage through water-cooled condenser 27 and introduction into accumulator 28.

Liquid condensate comprising diluent and monomer in accumulator 28 is removed by way of line 30 and a portion thereof is returned to distillation column 13 as reflux through line 31. The remainder of the condensate removed from accumulator 28 is passed by way of line 32 as feed to distillation column 33.

Distillation column 33 is operated under conditions such that a stream comprising monomer and some diluent is taken overhead by line 29 and passed through condenser 27 to condense diluent present in the overhead stream.

A side stream comprising diluent and monomer is removed from distillation column 33 by way of line 34, passed through water-cooled heat exchanger 35, and introduced into vessel 36 for storage and further handling. Bottoms removed from vessel 36 by way of line 37 are circulated through pump 38, water-cooled heat exchanger 39, and a portion passed through line 40 for recycle to either a homopolymerization or a copolymerization zone. The remainder of bottoms in line 37 is returned to vessel 36 by way of line 41. Distillation zone 33 is preferably operated under conditions such that approximately 75 to 80% of the monomer present in feed stream 10 is removed along with diluent in line 40.

A bottoms stream 42 comprising diluent substantially free of monomer is removed from distillation zone 33, passed through water-cooled heat exchanger 43, and introduced into vessel 44 for storage and further handling. A bottoms stream of diluent is removed from vessel 44 by way of line 45, passed through pump 46, water-cooled heat exchanger 47, and a portion is passed through line 48 for recycle either to a homopolymerization or a copolymerization zone. The remainder of diluent is returned to vessel 44 by way of line 49. A portion of bottoms stream 42 is used as reboiler heat for distillation zone 33 by passing a portion of the bottoms stream through steam-heated heat exchanger 50 and returning the heated stream to distillation 33 by way of line 51.

Referring to the drawing and accumulator 28, in particular, this vessel is provided with a column section 52 and refrigeration unit 53 for cooling and condensing the vapors exiting the system through vent 54. The vent stream 54 comprises light gases including ethylene monomer and other gases difficult to condense.

Makeup diluent such as isobutane is introduced into the system by way of line 55 into accumulator 28.

The following example is provided for the purpose of illustration only and is not intended to be unduly limiting the scope of the present invention.

EXAMPLE

This example gives details for a large-scale separation of a mixture comprising ethylene, 1-hexene and isobutane by means of two fractionators having common reflux.

Table I summarizes the composition and other pertinent parameters of various streams identified in the FIGURE.

TABLE I

| Stream No. Component | 12 | 26 | 24 | 15 | 31/32 | 55 | 54 | 40 | 48 |
|---|---|---|---|---|---|---|---|---|---|
| | | | | Composition (Mole Fraction) | | | | | |
| Hydrogen | .004 | .00319 | | | .00119 | | .10261 | | |
| Nitrogen | .007 | .00616 | | | .00397 | | .17956 | | |
| Methane | .0017 | .00188 | | | .00220 | | .03848 | .00025 | |
| Ethylene | .11605 | .11717 | | | .11473 | | .60483 | .11661 | |
| Ethane | .01201 | .01214 | | | .01198 | | .04050 | .01311 | |
| Propane | .0024 | .00244 | .00001 | | .00245 | | .00096 | .00284 | .00063 |
| N—Pentane | .00005 | .00018 | .00278 | .00086 | .0023 | .004 | .00000 | .00022 | .00038 |
| Isobutane | .81036 | .82407 | .23376 | .00792 | .83038 | .960 | .03255 | .83483 | .95571 |
| N—Butane | .03281 | .03277 | .03822 | .00205 | .03288 | .036 | .00050 | .03213 | .04329 |
| 1-Hexene | .01161 | | .62052 | .80862 | | | | | |
| N—Hexene | .002 | | .10472 | .18055 | | | | | |
| Total | 1.0000 | 1.0000 | 1.0000 | 1.0000 | 1.0000 | 1.0000 | 1.0000 | .10000 | 1.0000 |
| Lb-Moles/Day | 20641 | 29261 | 360 | 20 | 9000 | 400 | 805 | 16370 | 3486 |
| Temp., °F. | 218 | 172 | 114 | 362 | 104 | 100 | −11 | 110 | 114 |
| Pressure, Psia | 225 | 223 | 225 | 226 | 225 | 250 | 214.5 | 172 | 85 |
| Vapor Fraction | 1.0 | 1.0 | 0 | 0 | 0 | 0 | 1.0 | 0 | 0 |

Table II summarizes the most pertinent operating conditions in distillations column 13 and accessories.

TABLE II

| | |
|---|---|
| Feed Pressure, psia | 225 |
| Column Pressure, psia | 223 |
| Number of Theoretical Stages | 32 |
| Number of Actual Trays | 48 |
| Column Diameter, ft. | 4 |

TABLE II-continued

| | |
|---|---|
| Feed Point of Stream 12, Tray No. | 16 |
| Feed Point of Stream 31, Tray No. | 48 |
| Exit Point of Stream 18, Tray No. | 5 |
| Temperature at Bottom Tray, °F. | 361 |
| Temperature of Top Tray, °F. | 172 |
| Duty of Reboiler 16, MM BTU/Hr | 2.1 |
| Temperature of Reboiler 16, °F. | 362 |
| Temperature of Vessel 20, °F. | 114 |

Table III summarizes the most pertinent operating conditions in distillation column 33 and accessories.

TABLE III

| | |
|---|---|
| Feed Pressure, psia | 223 |
| Column Pressure, psia | 225 |
| Number of Theoretical Stages | 30 |
| Number of Actual Trays | 45 |
| Column Diameter, ft. | 3 |
| Feed Point of Stream 32, Tray No. | 45 |
| Exit Point of Stream 34, Tray No. | 19 |
| Exit Point of Stream 51, Tray No. | 1 |
| Temperature at Top Tray, °F. | 225 |
| Temperature at Bottom Tray, °F. | 190 |
| Duty of Reboiler 50, MM BTU/Hr | 1.4 |
| Temperature of Reboiler 50, °F. | 192 |
| Duty of Refrigeration Unit 53 MMBTU/Hr | −0.25 |
| Temperature of Refrigeration Unit 53, °F. | −11 |
| Duty of Condenser 27, MM BTU/Hr | −10 |
| Temperature in Accumulator 28, psia | 104 |
| Pressure in Accumulator 28, psia | 215 |
| Temperature in Vessel 36, °F. | 110 |
| Pressure in Vessel 36, psia | 172 |
| Temperature in Vessel 44, °F. | 114 |
| Pressure in Vessel 44, psia | 85 |

What is claimed is:

1. A process for the separation and recovery of a three-component, hydrocarbon-containing feed comprising olefin monomer, 1-olefin comonomer, and hydrocarbon diluent in two distillation zones having a common accumulation zone wherein the overhead streams from both distillations are combined, condensed and the condensate formed and passed to the common accumulation zone is divided into a feed portion for the second distillation and a reflux portion for the first distillation which comprises (a) passing said feed to a first distillation zone and therein subjecting same to distillation conditions sufficient to remove a bottoms stream comprising materials present in the feed heavier than said comonomer, a side stream comprising 1-olefin comonomer substantially free of other materials and an overhead vapor stream comprising olefin monomer and hydrocarbon diluent, (b) condensing said overhead vapor stream to form a condensate comprising diluent and monomer and passing said condensate to an accumulation zone, (c) removing condensate from said accumulation zone and passing at least a portion of said condensate as feed to a second distillation zone and passing the remainder of said condensate as reflux to an upper portion of said first distillation zone, (d) subjecting said portion of condensate in said second distillation zone to distillation conditions sufficient to remove a bottoms stream comprising diluent substantially free of olefin monomer, a side stream comprising hydrocarbon diluent and olefin monomer, and a overhead vapor stream comprising hydrocarbon diluent and olefin monomer, and (e) combining said overhead stream in (d) with said overhead stream in (a) prior to condensing in (b) and condensing the combined overhead streams and passing condensate thus formed to said accumulation zone in (b).

2. A process according to claim 1 wherein a portion of the combined overhead stream obtained in (e) is vented from the system from the accumulation zone in (b).

3. A process according to claim 1 wherein said olefin monomer is ethylene, propylene or 1-butene, said comonomer is a 1-olefin having 5–10 carbon atoms per molecule and said hydrocarbon diluent is a paraffinic hydrocarbon having a normal boiling point below that of the comonomer.

4. A process in claim 3 wherein said olefin is ethylene, said comomoner is 1-hexene and said hydrocarbon diluent is isobutane.

5. A process according to claim 4 wherein fresh makeup hydrocarbon diluent comprising isobutane is introduced into said accumulation zone.

6. A process according to claim 5 wherein the vapors present in said accumulation zone are subjected to refrigeration to condense and return condensibles comprising ethylene and diluent to the accumulation zone with the portion of the vapors that is not condensible being vented from the system.

7. A process according to claim 4 wherein said second distillation zone is operated under conditions of temperature and pressure such that approximately 75 to 80% of the ethylene recovered overhead in (a) is removed along with isobutane diluent in the side stream recovered in (d).

8. A process according to claim 7 wherein fresh makeup diluent comprising isobutane is introduced into said accumulation zone.

9. A process according to claim 8 wherein the vapors present in said accumulation zone are subjected to refrigeration to return condensables to the accumulation zone.

* * * * *